United States Patent [19]

Bollinger et al.

[11] 4,006,007
[45] Feb. 1, 1977

[54] N-(SUBSTITUTED PHENYL) DERIVATIVES OF SACCHARIN

[75] Inventors: Frederic G. Bollinger; John J. D'Amico, both of St. Louis, Mo.

[73] Assignee: Monsanto Company, St. Louis, Mo.

[22] Filed: Jan. 2, 1975

[21] Appl. No.: 537,989

[52] U.S. Cl. ................... 71/76; 71/72; 71/73; 71/77; 71/91; 71/103; 260/301; 260/518 A

[51] Int. Cl.² ................ A01N 5/00; C07C 101/48

[58] Field of Search .............. 260/515 M, 518 A; 71/103, 76

[56] References Cited

UNITED STATES PATENTS 3,658,892  4/1972  Martin et al. ............... 260/518 A
3,879,402  4/1975  Holland ...................... 260/518 A

OTHER PUBLICATIONS

Barkow, Chem. Absts., 6961c, vol. 61, (1964).
Andreu et al., Chem. Absts., 141185d, vol. 74, (1971).
Tanaka et al., Chem. & Pharm. Bull. 13(4), pp. 399–405 (1965).

*Primary Examiner*—James O. Thomas, Jr.
*Assistant Examiner*—G. T. Breitenstein
*Attorney, Agent, or Firm*—Richard H. Shear; Donald W. Peterson

[57] ABSTRACT

Certain derivatives of saccharin having the formula

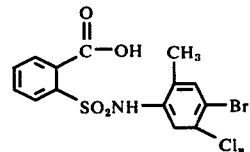

and

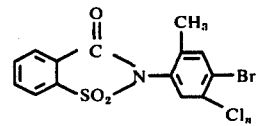

are found to regulate the growth of leguminous plants.

10 Claims, No Drawings

N-(SUBSTITUTED PHENYL) DERIVATIVES OF SACCHARIN

The invention relates to novel derivatives of saccharin that are found to be effective in regulating the growth of plants. More specifically, the invention relates to the use of the novel saccharin derivatives in the regulation of leguminous plant growth.

The saccharin derivatives of the invention can be represented by the formula

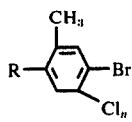

wherein
R is either

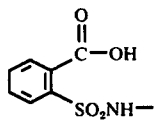 or 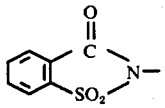

and $n$ is 0 or 1.

Representative of the saccharin derivatives found useful as plant growth regulants include:

I - o-(4-bromo-3-chloro-o-toluidinosulfonyl)-benzoic acid
II - o-(4-bromo-o-toluidinosulfonyl)benzoic acid
III - 1,1-Dioxide,2-(4-bromo-3-chloro-o-tolyl)-1,2-benzisothiazolin-3-one Generally, the compounds of the invention are prepared by reacting sulfobenzoic anhydride with the appropriate aniline in chloroform. In order to better illustrate the preparation of these compounds, the following examples are presented.

EXAMPLE 1

Preparation of o-(4-bromo-3-chloro-o-toluidinosulfonyl)-benzoic acid

To a stirred slurry containing 39.6 g. (0.2 mol.) of 93% o sulfobenzoic anhydride in 250 ml. of chloroform, 44 g. (0.2 mol.) of 4-bromo-5-chloro-2-methylaniline is added in one portion. An exothermic reaction causes a temperature rise from 24° to 39° C. After stirring at 25°–30° C. for 24 hours, the product is collected by filtration and air-dried at 25°–30° C. The product, m.p. 238°–242° C. with decomposition, is obtained in 98% yield.

Anal. Calcd. for $C_{14}H_{11}BrClNO_4S$: Found: C, 41.55; H, 2.74; N, 3.46; S, 7.92. C, 41.75; H, 3.40; N, 3.29; S, 7.34.

EXAMPLE 2

Preparation of o-(4-bromo-o-toluidinosulfonyl)benzoic acid

To a stirred slurry containing 19.8 g. (0.1 mol.) of 93% o-sulfobenzoic anhydride in 100 ml. of chloroform, 18.6 g. (0.1 mol.) of 4-bromo-2-methylaniline is added in one portion. An exothermic reaction causes a temperature rise from 21 to 38° C. After stirring at 25°–30° C. for 24 hours, the product is collected by filtration and air-dried at 25°–30° C. The product, m.p. 274°–276° C. with decomposition, is obtained in 84% yield. After recrystallization from methyl alcohol, it melted at 276°–277° C. with decomposition.

Anal. Calcd. for $C_{14}H_{12}BrNO_4S$: Found: C, 45.42; H, 3.27. C, 45.31; H, 3.51.

EXAMPLE 3

Preparation of o-(4-bromo-o-toluidinosulfonyl)benzoic acid

The procedure of Example 2 is followed replacing the 100 ml. of chloroform with 150 ml. of dioxane. The product obtained melts at 274°–276° C. with decomposition.

Anal. Calcd. for $C_{14}H_{12}BrNO_4S$: Found: C, 45.42; H, 3.27. C, 45.84; H, 3.60.

EXAMPLE 4

Preparation of 1,1-dioxide,2-(4-bromo-3-chloro-o-tolyl)1,2-benzisothiazolin-3-one A stirred slurry containing 19.8 g. (0.1 mol.) of 93% o-sulfobenzoic anhydride in 200 g. of Varsol, a naphthalenic based inert solvent, is heated to 140° C. for solution. At this temperature, 22 g. (0.1 mol.) of 4-bromo-5-chloro-2-methylaniline is added in one portion. The stirred reaction mixture is heated from 140° to 172° C. over a 4 hour period. After cooling to 30° C., the reaction slurry is stirred at 25°–30° C. for 24 hours. After cooling to 0° C., the product is collected by filtration and air-dried at 25°–30° C. The product, m.p. 225°–230° C. with decomposition, is obtained in 80% yield.

Anal. Calcd. for $C_{14}H_9BrClNO_3S$: Found: N, 3.62; S, 8.29. N, 3.18; S, 7.69.

As noted above, the novel saccharin derivatives are useful as plant growth regulants.

The term "plant regulant" or "plant growth regulant" as employed in this application, connotes a material which serves to modify the normal sequential development of a treated plant to agricultural maturity. Such modification may result from the effect of the material on the physiological processes of the plant or from the effect of said material on the morphology of the plant. It should additionally be recognized that modifications may also result from a combination or sequence of both physiological and morphological factors.

Regulation of plant growth or development is most readily observed as a change in the size, shape, color or texture of the treated plant or any of its parts. Similarly, changes in the quantity of the plant fruit or flowers are also quite apparent from simple, visual inspection. The above changes may be characterized as an acceleration or retardation of plant growth, stature reduction, leaf or canopy alteration, increased branching, tillering, terminal inhibition, increased flowering or fruit set, increased root growth, stool or sprout inhibition, delayed budding, defoliation, desiccation, delayed senescence, prolongated dormancy, increased cold hardiness, delayed or accelerated ripening, thinning of fruit, prevention of pre-harvest fruit drop, loosening of fruit and the like.

Modifications in the normal sequential development of a treated plant to agricultural maturity may also be manifested by reduced transpiration or increased carbohydrate deposition or protein content.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatures and are more resistant to pest infestations and to lodging. A darkening of the foliar color is illustrative of higher chlorophyll activity indicative of improved rate of photosynthesis. Further, a reduction in the maturation rate on portions of a crop permits an extended harvest period at peak yield and more efficient use of subsequent crop processing equipment.

It is to be understood that the regulation of plants in accordance with the instant invention does not include the total inhibition or the killing of such plants. Although phytotoxic amounts of the materials disclosed herein might be employed to exert a herbicidal action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

In accordance with this invention it has been found that desirable modification of plants is achieved by applying the above-described plant regulants to seeds, emerging seedlings, roots, stems, leaves, flowers, fruits or other plant parts. Such application may be made directly to the plant part, or indirectly by application to the plant growing medium.

The term "active ingredient" is used hereinafter to describe the active saccharin derivatives described above.

In practicing the plant growth regulating methods of this invention, the active ingredient can be used alone or in combination with a material referred to in the art as an adjuvant in liquid or solid form. The plant growth regulating compositions of this invention are prepared by admixing the active ingredient with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely divided particulate solid, a solvent liquid of organic origin, water, a wetting agent, dispersing agent, or emulsifying agent or any suitable combination of these.

Illustrative finely divided solid carriers and extenders which are useful in the plant growth regulating compositions of this invention, include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents include, for example, Stoddard solvent, acetone, alcohols, glycols, ethyl acetate, benzene and the like. The plant growth regulating compositions of this invention, particularly liquids and wettable powders, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The compositions can also be applied from airplanes as a dust or spray. The application of the plant growth regulating compositions to the plant growth medium is generally carried out by incorporating the compositions in the soil or other media in the area where modification of the plants is desired.

In selecting the appropriate non-toxic rate of application of the active ingredient it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts from about 0.05 to about 10 or more pounds per acre. Foliar applications of from 0.1 to 5 pounds of the active ingredient per acre are preferred. In applications to the soil habitat of germinant seeds, emerging seedlings, and established vegetation for the regulation of plant growth, the active ingredients are applied in amounts of from about 0.01 to about 20 pounds per acre or more. Preferably, the active ingredients are applied to the soil at a rate of from 0.1 to 10 pounds per acre. Foliar application to plants beginning to blossom are particularly advantageous and are preferred.

As stated above, the novel saccharin derivatives are useful in regulating the growth of leguminous plants, as represented by the soybean plant. The practice of this invention provides means for obtaining plants of reduced stature. The method of the present invention can be conveniently carried out to obtain plants of reduced stature without substantial injury to the plants.

In accordance with the practice of the invention, several plant growth regulating compositions were formulated utilizing various saccharin derivatives as the active ingredient. These compositions were formulated so that they would be applied at a rate the equivalent of 200 gallons per acre (1900 liters/hectare). Table I illustrates the formulation of the composition for several application rates of active ingredient. In each formulation, the stock solution utilized is 1% of the active ingredient dissolved in acetone.

TABLE I

| RATE LBS/ACRE | (KILOS/HECTARE) | ml. of 1% Stock Solution | ml. Acetone | ml. of 0.39% TWEEN 20 in Water as Surfactant |
| --- | --- | --- | --- | --- |
| 6.0 | (6.72) | 2.0 | — | 3.6 |
| 5.0 | (5.60) | 2.0 | 1.0 | 3.7 |

TABLE I-continued

| RATE LBS/ACRE | (KILOS/HECTARE) | ml. of 1% Stock Solution | ml. Acetone | ml. of 0.39% TWEEN 20 in Water as Surfactant |
| --- | --- | --- | --- | --- |
| 2.5 | (2.80) | 1.0 | 2.0 | 3.7 |
| 1.2 | (1.34) | 0.4 | 1.6 | 3.6 |
| 1.0 | (1.12) | 0.4 | 2.6 | 3.7 |

Utilizing the saccharin derivatives of the invention, as the active ingredient, various compositions were formulated in accordance with TABLE I which showed unexpected plant growth regulatory properties as demonstrated by the following examples.

EXAMPLE 5

A number of soybean plants, variety Corsoy, are grown from seeds in aluminum pans in a greenhouse for a period of approximately 1 week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. The aqueous composition of the chemical is then applied to the pan of growing plants by overhead spray at a desired rate. The treated pans, along with the control pans, are maintained in a greenhouse and watered from below on a sand bench and fertilized with a uniform portion of a water-soluble balanced fertilizer.

Two weeks after application of the chemical the average height of the soybean plants in the treated pan is again measured as above and the difference in the average height before and 2 weeks after application represent the increase in the development of the treated plants. This development in growth of the treated plants is compared to the average increase in growth of the plants in the control pans during the same period of time. A variation of 25% or more in the development of at least two-thirds of the treated plants when compared to the development of the control plants demonstrates that the chemical is an effective plant regulant. Thus, a chemical is considered active when the treated plants manifest a decrease in growth of at least 25% less than that of the control plants, i.e., stature reduction or an increase in growth in excess of 25% of that of the control plants, i.e., growth stimulation.

Results obtained when various saccharin derivatives are used as the active ingredient in Example 5 are summarized in TABLE II.

TABLE II

| Cmpd. | RATE (lbs/acre) | RESULT |
| --- | --- | --- |
| I | 6.0 | Stature Reduction, Axillary Bud Development, Altered Canopy |
| | 3.0 | Axillary Bud Development, Altered Canopy |
| | 1.2 | Axillary Bud Development, Altered Canopy |
| II | 6.0 | Stature Reduction, Axillary Bud Development |
| III | 6.0 | Stature Reduction, Axillary Bud Development, Altered Canopy |
| | 3.0 | Axillary Bud Development |

EXAMPLE 6

Individual soybean plants, variety Wayne, are grown from seed in 6 inch pots containing a good grade of top soil. Two pots of 6-week old plants (5–6 trifoliate stage) are used for each application of the chemical. An overhead spray of an aqueous composition of the chemical is applied to the pots at an equivalent rate as indicated below. Two to four sets of plants which received no chemical application are included and serve as controls. All of the pots are maintained under good growing conditions and are watered and are uniformly fertilized with a uniform amount of a water-soluble balanced fertilizer. Two weeks after the application of the chemical the growth response of the treated plants are compared with that of the control plants. The total height of the plant is measured to the tip of the terminal bud. A variation of 15% in the average total height of the treated plants, when compared to the average total height of the control plants, demonstrate that the chemical is an effective plant growth regulator. Observations on other plant modification, e.g., canopy shape, axillary bud development and the like are noted.

Results obtained when the various saccharin derivatives of the invention are used as the active ingredient in Example 6 are summarized in TABLE III.

TABLE III

| Cmpd. | RATE (lbs/acre) | RESULT |
| --- | --- | --- |
| I | 5.0 | Stature Reduction, Axillary Bud Development, Altered Canopy |
| II | 5.0 | Early Pod Set, Chlorosis, Leaf Distortion, altered Canopy |
| | 2.5 | Chlorosis, Leaf Distortion |
| III | 5.0 | Early Pod Set, Enhanced Pod Set |
| | 2.5 | Stature Reduction, Axillary Bud Development, Delayed Pod Set |
| | 1.0 | Axillary Bud Development, Enhanced Pod Set |

Stature reduction was also found when soybean plants of the Wayne variety were planted at a seeding rate of 180,000 plants per acre (72,000 plants per hectare) in 20-inch (50 cm) rows and treated with a foliar application of o-(4-bromo-3-chloro-o-toluidinosulfonyl)benzoic acid at rates of 0.5, 2.0 and 4.0 pounds per acre. Each treatment was replicated four times with observations being made 2 weeks and 4 weeks after treatment.

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

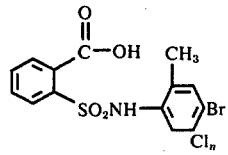

wherein n is 0 or 1.

2. The compound of claim 1 in which is o-(4-bromo-3-chloro-o-toluidinosulfonyl)benzoic acid.

3. The compound of claim 1 which is o(4-bromo-o-toluidinosulfonyl)benzoic acid.

4. A method of regulating the growth of leguminous plants which comprises treating said plants with a retardative amount of a compound of the formula

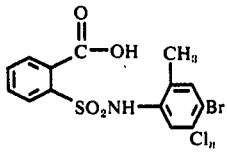

wherein $n$ is 0 or 1.

5. A method according to claim 4 wherein said compound is o-(4-bromo-3-chloro-o-toluidinosulfonyl)benzoic acid.

6. A method according to claim 4 wherein said compound is o-(4-bromo-o-toluidinosulfonyl)benzoic acid.

7. A method according to claim 4 wherein said plants are soybean plants.

8. A composition for the growth regulation of leguminous plants comprising an adjuvant and an effective amount of a compound of the formula

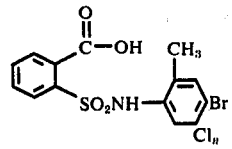

wherein $n$ is 0 or 1.

9. A composition according to claim 8 wherein said compound is o-(4-bromo-3-chloro-o-toluidinosulfonyl)benzoic acid.

10. A composition according to claim 8 wherein said compound is o-(4-bromo-o-toluidinosulfonyl)benzoic acid.

* * * * *